United States Patent [19]

Rademacher et al.

[11] Patent Number: 5,164,374

[45] Date of Patent: Nov. 17, 1992

[54] USE OF OLIGOSACCHARIDES FOR TREATMENT OF ARTHRITIS

[75] Inventors: Thomas W. Rademacher; Raymond A. Dwek, both of Oxford, United Kingdom

[73] Assignee: Monsanto Company, St. Louis, Mo.

[21] Appl. No.: 629,600

[22] Filed: Dec. 17, 1990

[51] Int. Cl.$^5$ .................. A61K 31/70; A61K 31/715
[52] U.S. Cl. ........................ 514/23; 435/18; 436/94; 436/501; 436/506; 436/509; 436/827; 536/1.1; 536/4.1; 514/825; 514/885
[58] Field of Search ............ 514/825, 885, 23; 536/1.1, 4.1; 435/18; 436/94, 501, 506, 509, 827

[56] References Cited

U.S. PATENT DOCUMENTS

| | | | |
|---|---|---|---|
| 3,865,801 | 2/1975 | Chiba et al. | 530/397 |
| 4,659,659 | 4/1987 | Rademacher et al. | 435/18 |
| 5,034,516 | 7/1991 | Roy et al. | 536/4.1 |
| 5,037,969 | 8/1991 | Minami et al. | 536/1.1 |
| 5,047,337 | 9/1991 | Li et al. | 435/129 |

FOREIGN PATENT DOCUMENTS

88/09933  12/1988  PCT Int'l Appl.

OTHER PUBLICATIONS

Witt et al., Nutr. Metab. 23, 51–61 (1979).
Murray & Brown, J. Immunol. 141, 2068–2073 (1988).
Pearson and Jamnejad, ICSU Short-Rep. 2 (Adv. Gene Tech.), 269–270 (1985).
Weis et al., Nature 333, 426–431 (1988).
Pekelharing et al., Ann. Rheum. Dis. 47, 91–95 (1988).
Stanworth & Henney, Immunol. 12, 267–274 (1967).
Schifferli et al., New Engl. J. Med. 315, 488–495 (1986).
Jaffe, J. Lab. Clin. Med. 60, 409–421 (1962).
Walker Labs. Ltd., Melisa Rheumatoid HAII Immunoassay Kit, Product Insert, 1988.

Primary Examiner—Ronald W. Griffin
Attorney, Agent, or Firm—Scott J. Meyer

[57] ABSTRACT

A method for the treatment of arthritis or a related autoimmune disease that exhibits immune complexes in serum or synovial fluid is provided which comprises exposure of the serum or synovial fluid to an oligosaccharide containing a structural component that inhibits or disrupts the degree of occupancy of the Fc carbohydrate binding site on IgG, e.g., sialyllactose.

11 Claims, 9 Drawing Sheets

RA-

RA+

USE OF OLIGOSACCHARIDES FOR TREATMENT OF ARTHRITIS

BACKGROUND OF THE INVENTION

This invention relates to compositions and method for the treatment of arthritis and related autoimmune diseases.

A known feature of autoimmune diseases is the presence of immune complexes. Immune complexes help eliminate foreign bodies such as microorganisms. In patients with diseases associated with immune complexes, the formation of the immune complex can be a malfunction of the normal system whereby in some cases the antibody response is directed against native material (self-antigen). In other cases the immune response is directed against the foreign substance repeatedly introduced into the system.

In rheumatoid arthritis, for example, the chronic inflammation of the synovial membrane of affected joints, as well as many of the extra-articular manifestations of the disease, have been ascribed to immune complexes (either localized in the joint or circulating). The immune complexes in patients with rheumatoid arthritis consist of IgG homopolymer complexes [i.e. IgG-(IgG)n, self-associated] or heteropolymers [i.e. IgM-(IgG)n], thereby suggesting that the immunoglobulins are both the antigen and the antibody. In addition, complement components are frequently bound to these complexes. The IgG molecules found in the complexes are referred to as IgG-rheumatoid factor (IgG-RF) while the IgM molecules in the complexes are called IgM-rheumatoid factors (IgM-RF).

In rheumatoid arthritis it has long been postulated that auto-sensitization to IgG may play a pivotal role in the pathogenesis of the disease, and immune complexes are formed through the binding of the IgM, IgG, or IgA rheumatoid factors to the constant region domains of IgG molecules. The immunogenic site on IgG has been localized to the Fc moiety, but there is no evidence for amino acid changes in the Fc of this IgG. Data on the carbohydrate composition of IgG present in the intermediate complexes isolated from the serum of patients with rheumatoid arthritis invariably show an increased level of sialic acid (usually Fab-associated) as compared to normal serum IgG [Hymes and Mullinax, *J. Biol. Chem.* 254, 3148 (1979); and Hansson et al., *Scand. J. Immunol.* 13, 57 (1981)], and decreased content of Fc-associated galactose [Hymes and Mullinax, supra]. In one case, this sialic acid was shown to occur on light chains, and was crucial for IgG self-association, since its removal by neuraminidase treatment abolished complex formation [Hymes and Mullinax, supra]. In a recent study [Pekelharing et al , *Ann. Rheum. Dis.* 47, 91 (1988)] it was found that serum IgG from patients with rheumatoid arthritis had a lower carbohydrate content and therefore presumably lower Fab N-glycosylation, consistent with the sequestration into complexes of IgG enriched in Fab N-glycosylation. Together, these observations suggest that immune-complex formation in rheumatoid arthritis could involve both Fab N-glycosylation and agalactosyl structures in the Fc. The molecular mechanism whereby these two factors might contribute to IgG auto-antigenicity or self-association are not known, but a study of the crystal structure of Fc provides some insight into this. The crystal structure [Sutton and Phillips, *Biochem. Soc. Trans.* 11, 130 (1982)] clearly indicates that each N-linked oligosaccharide in the Fc can interact with the protein surface of the CH2 domain, principally via the (NeuNAc$\alpha$2→6-)Gal$\beta$→4 segment of the Man $\alpha$→6 arm. This is the principal non-covalent protein-oligosaccharide interaction in Fc, and serves to restrain the Fc oligosaccharides, and also to mask certain underlying Fc polypeptide determinants. It is therefore suggested that the change in the degree of occupancy of the Fc carbohydrate-binding site, secondary to decreased outer-arm galactosylation of Fc oligosaccharides, could lead to IgG self-association through one of the following mechanisms. First, through the insertion into this vacant site of an appropriate Fab-linked oligosaccharide from another IgG molecule. Second, through the interaction of the affected IgG with either naturally occurring or induced anti-GlcNAc antibodies. Third, through interaction of the affected IgG with antibodies induced against the peptide (or peptide-oligosaccharide) epitopes previously largely masked by the native oligosaccharide. Self-association of IgG could occur by any of these mechanisms. Further, occupation of the vacant oligosaccharide-binding site by other serum or synovial fluid glycoprotein or cartilage components can also be envisaged.

Additional background information concerning glycosylation patterns in serum IgG of rheumatoid arthritis patients can be had by reference to the following four recent publications:

Parekeh et al., "Association of Rheumatoid Arthritis and Primary Osteoarthritis with Changes in the Glycosylation Pattern of Total Serum IgG," *Nature* 316, 452-457 (1985).

Parekh et al., "Galactosylation of IgG Associated Oligosaccharides: Reduction in Patients with Adult and Juvenile Onset Rheumatoid Arthritis and Relation to Disease Activity," *Lancet i*, 966-969 (1988).

Parekh et al., "A Comparative Analysis of Disease-Associated Changes in the Galactosylation of Serum IgG," *J. of Autoimmunity* 2, 101-114 (1989).

Rademacher et al., "The Role of IgG Glycoforms in the Pathogenesis of Rheumatoid Arthritis," *Springer Seminars in Immunopathology* 10, 231-249 (1988).

A recent publication by Pearson and Jamnejad, *ICSU Short Rep.*, 2 (*Adv. Gene Technol.*), 269-270 (1985), reported that when rheumatoid factor IgM is incubated with sialyl-N-acetyl-lactose as an additional step in a conventional ELISA test, there was less subsequent interaction with the normal antigen IgG. However, no data are given and the naming of the sugar compound is indefinite. The reported conclusions were that rheumatoid factor from some patients may be specifically blocked by the sialyl-N-acetyl-lactose and that the enzyme galactosyl transferase thus may be involved in the etiology of rheumatoid arthritis.

The known relationships between sialyloligo-saccharides and rheumatoid arthritis can be summarized as follows: N-acetylneuraminosyl oligosaccharides of great structural diversity are the major constituents of human milk. That these structures may be important comes from the studies of Witt et al. [*Nutr. Metab.* 23, 51-61, (1979)] who suggested that these oligosaccharides were not just storage forms of sialic acid but were absorbed and distributed to the tissues intact. Since these studies, it has also become evident that sialyloligo-saccharides are important as bacterial anti-adhesions, preventing infection in the newborn.

The urinary excretion of sialyloligosaccharides is known to increase during pregnancy. Interestingly, there is a pregnancy dependence for the excretion of sialyl N-acetyl-lactosamine isomers in urine in contrast to sialyl lactose containing isomers in human milk. The blood serum levels have not been measured. Urinary sialyloligosaccharide excretion can be used as an indicator of disease activity in patients with rheumatoid arthritis [*Rheumatol. Int.* 1, 7-10, (1981); *Eur. J. Clin. Invest.* 8, 405-409 (1978)]. Both the urinary excretion of sialyl-lactose and sialyl-N-acetyllactosamine isomers are increased in the disease.

More recent studies have shown that sialyl lactose and sialyl-N-acetyllactosamine may be low-molecular weight acute phase reactants [*Ann. of Rheum. Dis.* 41, 268-271 (1982)]. In this comparative study rheumatoid arthritis (RA) patients, with active, aggressive RA had a significantly higher urinary sialyl lactose content, serum CRP and SAA levels than patients with mild disease. In SLE, while sialyl lactose excretion was elevated relative to controls, the excretion correlated neither with serum CRP nor with SAA. This suggests the specific control mechanisms operate for the synthesis of sialyloligosaccharides in RA and pregnancy.

Still more recently, sialyloligosaccharides containing inositol have been found in pregnancy urine [*Carb. Res.* 115, 221-229 (1983)].

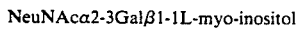
NeuNAcα2-3Galβ1-1L-myo-inositol

Their excretion by non-pregnant individuals has not yet been reported.

Research into 'factors' from the urine of pregnant women was initiated in the 1940's by Hench in his search for the pregnancy factor which causes the remission of arthritis in pregnant women [*Mayo Clin. Proc.* 24, 167-178, (1949)]. His fractionation of urine led to the eventual discovery of cortisone. Subsequent studies, however, showed that cortisone was not the elusive pregnancy 'factor', which still remains chemically undefined today.

BRIEF DESCRIPTION OF THE INVENTION

In accordance with the present invention, compositions and method for the treatment of arthritis and related autoimmune diseases are provided. The method comprises treating the immune complexes in a body fluid such as serum or synovial fluid by exposure to an oligosaccharide containing a structural component that inhibits or disrupts the degree of occupancy of the Fc carbohydrate binding site on IgG.

In accordance with conventional nomenclature, the Fc is the crystallizable fragment of the antibody molecule obtained by papain digestion as distinguished from the Fab or antigen-binding fragment.

The preferred oligosaccharides for use in the method of invention are trisaccharides which contain either a reducing terminal glucose or N-acetylglucosamine (GlcNAc) residue substituted with the disaccharide N-acetylneuraminyl α→3(6) galactopyranose (i.e. NeuNAcα3(6)GalΘ,→). These oligosaccharides are illustrated by the trisaccharide N-acetylneuraminyl α→3(6) galactose β→4 glucose, also referred to as sialyllactose, where the galactose and glucose residues are in the D-pyranose configuration.

Sialyllactose is commercially available and also occurs naturally in human milk and bovine colostrum in mixtures of the (2→3) and (2→6)-β-D-galactopyranosyl isomers. In bovine colostrum the mixture is about 83% (2→3) or 3' isomer and 9% (2→6) or 6' isomer; whereas in human milk these isomers exist substantially in the reverse proportions. These commercially available mixtures generally also contain a small amount of 2,6(3)-sialyllactosamine. See, e.g., Table I, below. These oligosaccharide compounds are also found in the urine [Derappe et al., *Carbohyd. Res.* 145, 341-347 (1985)] and serum [Example 4 hereinafter] of pregnant women.

The effectiveness of the sialyllactose in disrupting or disaggregating immune complexes in the serum and synovial fluid of rheumatoid arthritis patients is demonstrated by comparison with other sugars such as the monosaccharides, glucose, N-acetylglucosamine, N-acetylneuraminic acid (sialic acid) and galactose, and the disaccharide, N-acetyllactosamine, which were ineffective.

DETAILED DESCRIPTION OF THE INVENTION

While the specification concludes with claims particularly pointing out and distinctly claiming the subject matter regarded as forming the present invention, it is believed that the invention will be better understood from the following description taken in conjunction with the accompanying drawings in which, briefly:

FIG. 4 also should be compared with FIGS. 5-6.

Figure 1A:
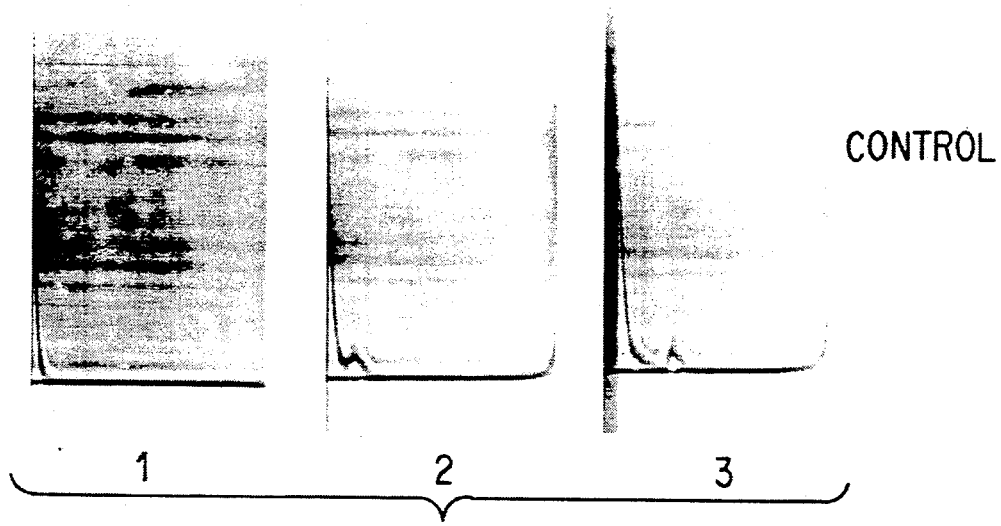
FIGS. 1a, 1b and 1c show the ultracentrifuge analysis of (1a) serum from a normal person (Control); (1b) serum from a patient with rheumatoid arthritis (RA−); and (1c) serum from the same rheumatoid arthritis patient treated with bovine sialyllactose (Sigma mixture, see Table I, below) (RA+) in an embodiment of the invention.

As illustrated by the results shown in these figures, the effectiveness of oligosaccharides to inhibit or disrupt the formation of immune complexes can be determined by several methods such as, e.g., a) ultracentrifuge analysis;
b) quantitative precipitin test; and
c) enzyme-linked immunosorbent assay.

In the ultracentrifuge analysis, the oligosaccharide-treated serum or synovial fluid of a rheumatoid arthritis patient is compared to rheumatoid arthritis control samples which have not been thus treated and with samples from a normal person. The γ-globulin in a normal person will exhibit a sedimentation rate or velocity 7S which is indicative of monomeric IgG. The sample from a rheumatoid arthritis patient will have a fast-sedimenting material. According to Stanworth and Henney, *Immunology* 12, 267-274 (1967), the IgG-containing complexes in patients with rheumatoid arthritis can range from 11S to >100S. In the oligosaccharide-treated samples from rheumatoid arthritis patients, this fast-sedimenting material will disappear and be converted essentially to 7S.

The quantitative precipitin test for rheumatoid arthritis is based essentially on serologic reactions. According to this test, the patient's serum is reacted with a variety of serological systems, all of which contain γ-globulin in some form or a component of Cohn Fraction II obtained from plasma or serum, which is largely γ-globulin [Cohn et al., *J. Clin. Invest.* 23, 417-432 (1944); Cohen et al., *J. Amer. Chem. Soc.* 68, 459-475 (1946)]. If the patient's serum is positive for rheumatoid arthritis, the presence of the so-called rheumatoid factor will cause the agglutination or immunoprecipitation reaction which can be compared with normal control samples.

In the quantitative precipitin test, the rheumatoid factor preferably reacts with the γ-globulin which has been heat aggregated to form an equivalence precipitate. This test is further described, for example, by Jaffe, *J. Lab. Clin. Med.* 60 (3), 409-421 (1962).

In the quantitative precipitin test as used herein, the oligosaccharide-treated serum or synovial fluid of a rheumatoid arthritis patient is compared to the rheumatoid arthritis sample without such treatment and/or control samples from a normal patient.

In a conventional enzyme-linked immunosorbent assay (ELISA), an antigen or antibody is linked to an insoluble carrier surface. The thus sensitized carrier surface captures the corresponding antibody or antigen from the test solution (e.g., serum). An enzyme-labelled antiglobulin attaches to the antigen or antibody complex, which is detected by the enzyme label changing the color of an added substrate. The optical density of the final color is directly proportional to the amount of unknown antibody or antigen in the original test solution. See, e.g., Engvall and Perlmann, *Immunochemistry* 8, 871-874 (1971); *J. Immunol.* 109, 129-135 (1972).

In a typical ELISA procedure, horseradish peroxidase is used as the labeling enzyme and o-phenylenediamine is used as the peroxidase substrate. The reactions are conveniently carried out in plastic microplate wells in which the colorimetric end-point is determined by a spectrophotometric reading at, e.g., 492 nm. The optical density can be plotted against concentration of the known antibody linked to the carrier and the concentration of the unknown read from a standard curve.

An ELISA test for rheumatoid arthritis is illustrated hereinafter (Example 3) by use of the commercially-available Melisa Rheumatoid HAII (human anti-immunoglobulin immunoglobulins) Immunoassay Kit from Walker Laboratories Ltd., Cambridgeshire, England. The reagents in this kit react equally with all immunoglobulin classes, whereby it measures IgG plus IgM rheumatoid factors. See, e.g., Gioud-Paquet et al., *Annals of the Rheumatic Diseases* 46, 65-71 (1987), and PCT Inter. Appln. WO 88/09933, published Dec. 15, 1988. This kit uses IgG coated onto a micropin solid phase and peroxidase labelled IgG as the enzyme blank. Serum samples are mixed with the labelled IgG and allowed to interact with the micropins. Rheumatoid factors cross link the labelled IgG with the solid phase IgG. In the absence of rheumatoid factors, label cannot bind, thereby giving very low assay blanks. The enzyme substrate in this test is o-phenylenediamine-HCl in citrate buffer and horseradish peroxidase is used as the enzyme.

The following detailed examples on the use of sialyllactose for the treatment of serum and synovial fluid from rheumatoid arthritis patients will further illustrate the invention although it will be understood that the invention is not limited to these specific examples.

EXAMPLE 1

Human blood serum (about 400 μl) was dialysed at 4° C. for 3 hours against a buffer composed of 20 mM sodium phosphate/0.1M NaCl, pH 7.4, containing 0.005% sodium azide, using a BRL continuous-flow dialysis apparatus (Bethesda Research Laboratories). Serum was then diluted with an equal volume of this buffer and centrifuged rapidly (about 10 minutes) at room temperature through a 0.5 μm Teflon ® filter. Half of the diluted serum was raised to 10 mM in sialyllactose/lactosamine, pH 7.4, (mixed isomers from bovine colostrum, Sigma Chemical Company), and an equal volume of buffer was added to the other half of the diluted serum. Both samples were incubated at 37° C. for 12 hours and then subjected to ultracentrifuge analysis (Beckman Ultracentrifuge, Model E, fitted with a schlieren optical system). Runs were performed at 20° C. and 59,200 rpm. Photographs were taken at 6 minute intervals. A control sample from a normal healthy person with very little high molecular weight was also run.

Figure 1B:
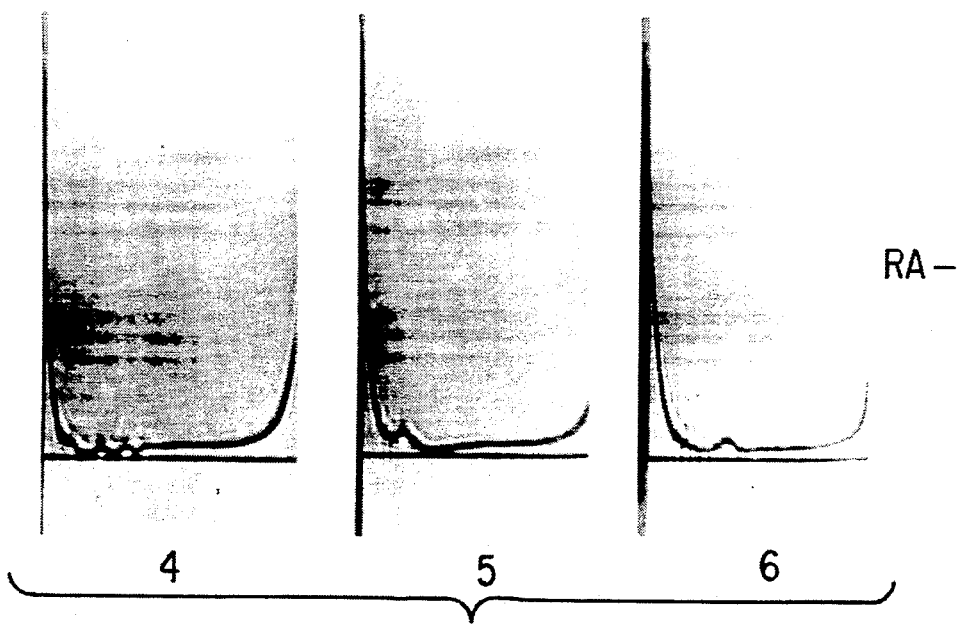
Figure 1C:
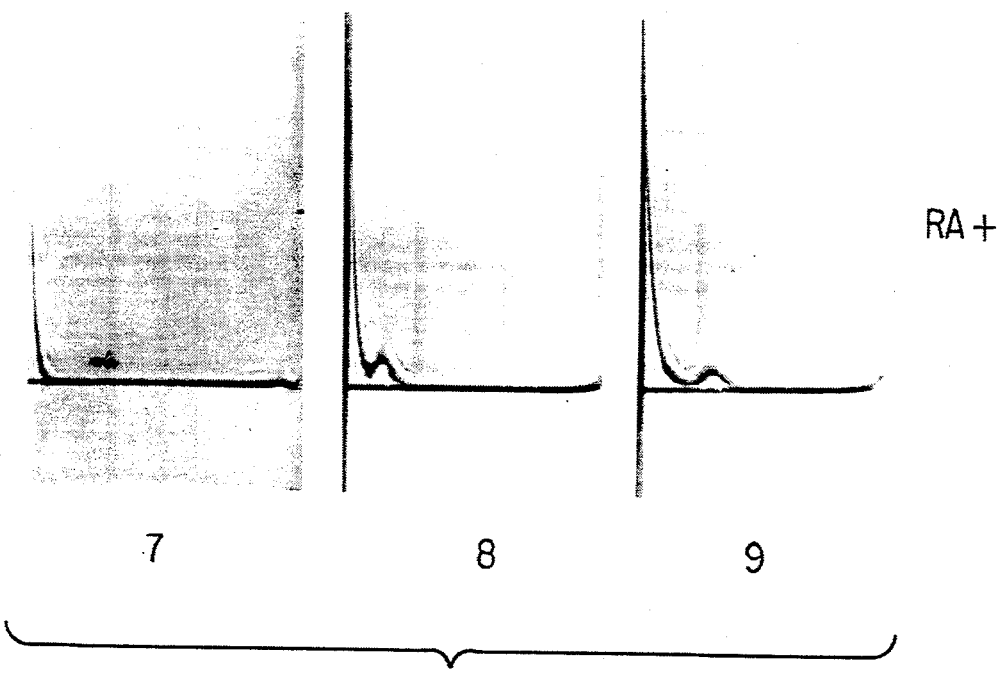
Figure 2A:
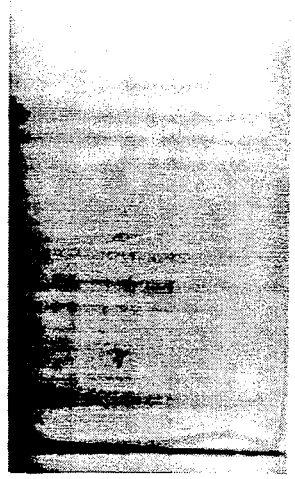
FIGS. 2a and 2b show the ultracentrifuge analysis of the serum from a second patient with rheumatoid arthritis (2a) without (RA−) and (2b) with (RA+) treatment by bovine sialyllactose as in FIG. 1.
Figure 2A:
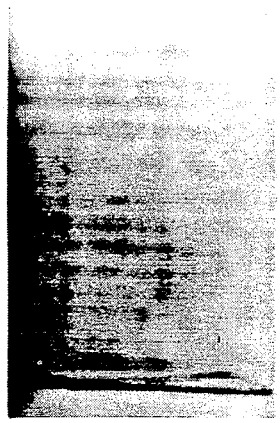
Figure 2A:
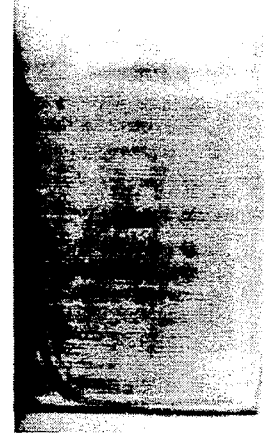
Figure 2B:
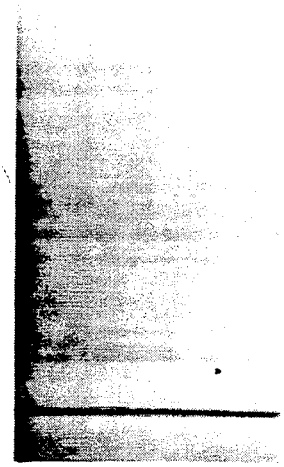
Figure 2B:
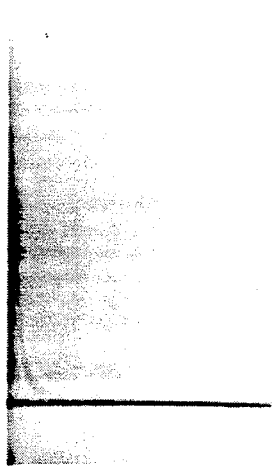
Figure 2B:
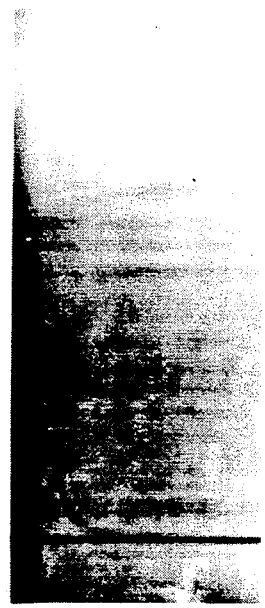
Figure 3A:
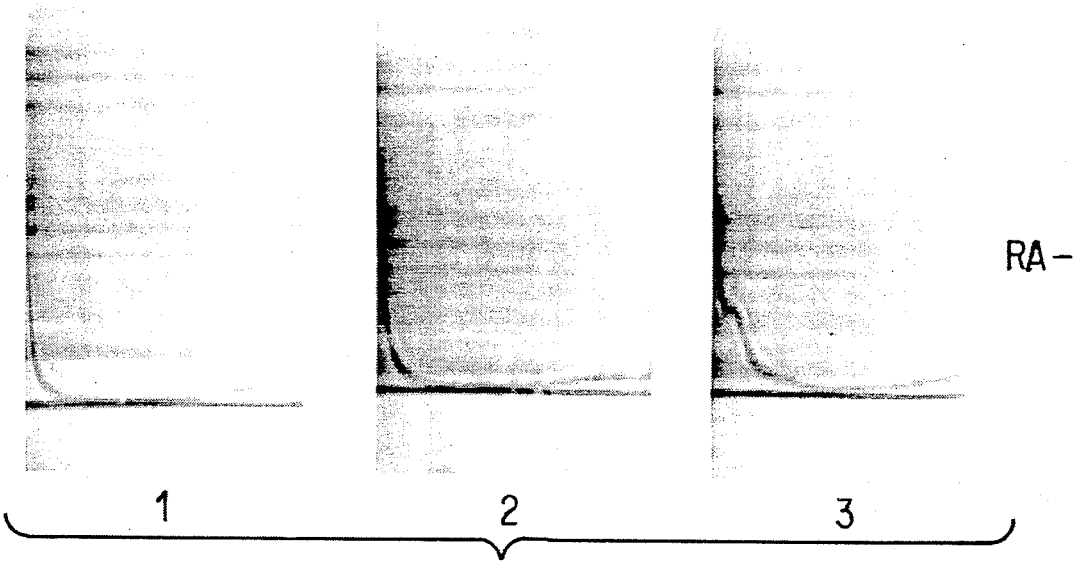
FIGS. 3a and 3b show the ultracentrifuge analysis of the serum from a third patient with rheumatoid arthritis (3a) without (RA−) and (b) with (RA+) treatment by bovine sialyllactose as in FIG. 1.
Figure 3B:
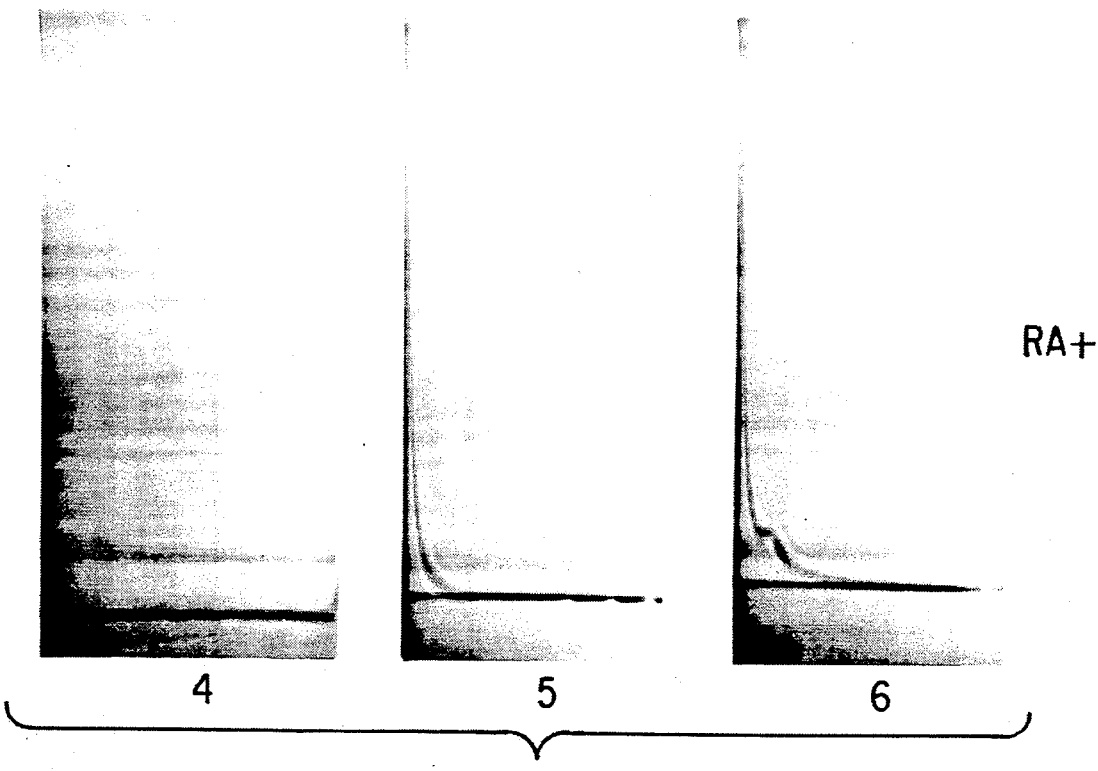

The results from the sera of 3 patients with rheumatoid arthritis are shown in FIGS. 1 to 3. Three time frames are shown for each sample (at 6 minutes, 12 minutes and 18 minutes, respectively, left to right). The small peak moving away from the meniscus is of sedimentation velocity 7S, and therefore monomeric IgG. There is very little faster sedimenting material in the control sample (FIG. 1a), but a considerable amount of fast sedimenting material in the serum samples from patients with rheumatoid arthritis (FIGS. 1b, 2a, 3a). Some of this larger material is discrete, and some is very large. Most of this fast sedimenting material disappears upon incubation with sialyl-lactose and the serum has been converted to normal (FIGS. 1c, 2b, 3b). Of particular interest is the observation that the 7S peak generally has a greater area after incubation with sialyllactose then before, implying that the fast sedimenting material contains IgG which can be dissociated from the complexes with sialyllactose.

It is thus seen that in the ultracentrifuge analysis, IgG has been dissociated from rheumatoid factor complexes by siallylactose at physiological pH.

EXAMPLE 2

Heat aggregated IgG was prepared by heating Cohn Fraction II to 63° for 15 minutes. Increasing amounts of heat aggregated IgG were added to a constant volume of the sample being tested. The reaction mixture was incubated for 4 hours at 37° C. and retained for 16 hours at room temperature to allow the equivalence precipitate to form. The supernatants were removed after centrifugation; the precipitates were washed twice with phosphate buffered saline and dissolved in 1M NaOH. The optical density (OD) or absorbance at 280 nM of the resulting solution was plotted against the amount in milligrams of heat aggregated IgG from which they were derived.

The following samples were tested:

(a) Human blood serum containing rheumatoid factor complexes was dialysed against 0.1M sodium acetate, pH 3.5, to dissociate the complexes. Half of the sample was made 10 mM in sialyllactose (pH 3.5) and then returned to pH 7 with sodium hydroxide. The other half had an equivalent amount of phosphate buffered saline (PBS) added instead of sialyllactose and was also returned to pH 7 with sodium hydroxide.

Figure 4:
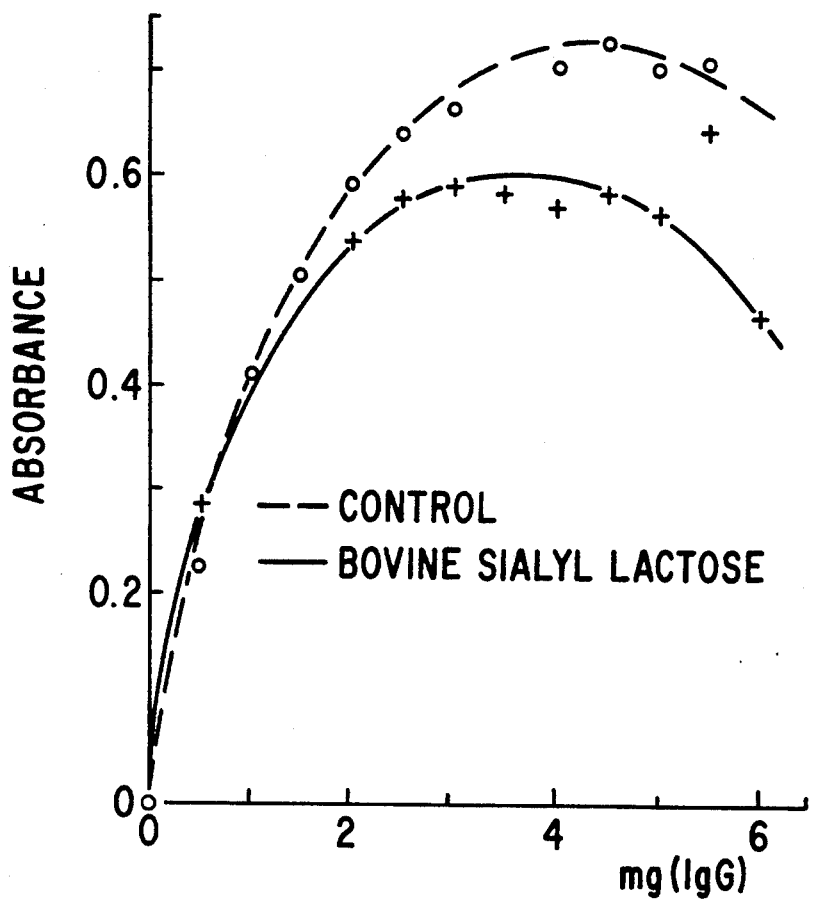
FIG. 4 is a graphical representation which shows precipitin curves that demonstrate the effectiveness of bovine sialyllactose compared to a control (no siallyllactose) on the binding of rheumatoid factor complexes to heat aggregated IgG in another embodiment of the invention.
Figure 5:
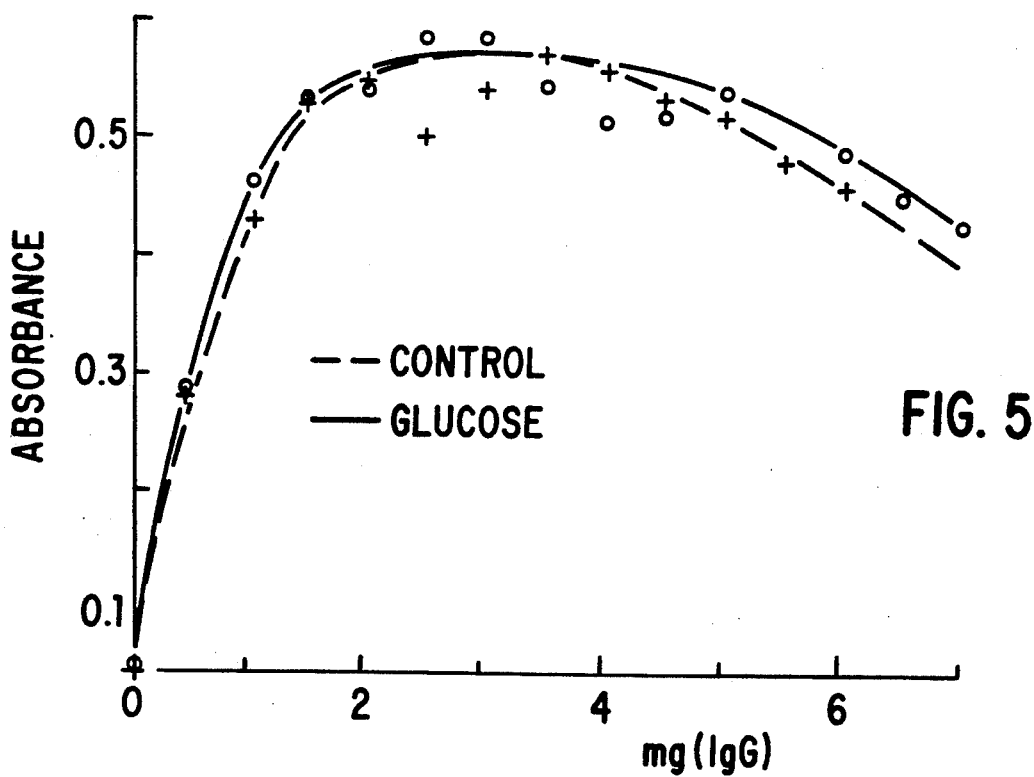
FIG. 5 is a graphical representation which shows precipitin curves that demonstrate the ineffectiveness of glucose compared to a control (no glucose) on the binding of rheumatoid factor complexes to heat aggregated IgG.
Figure 6A:
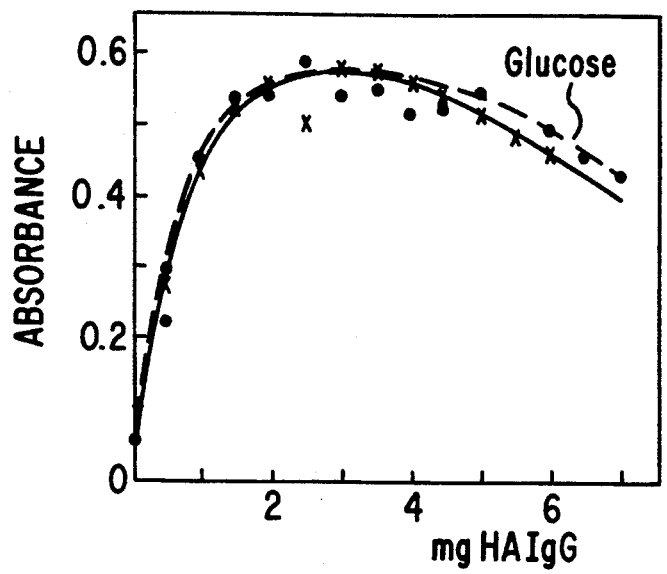
FIGS. 6A, 6B, 6C, 6D and 6E are graphical representations which show the precipitin curves that demonstrate that (6A) glucose, (6B) N-acetyllactosamine, (6C) N-acetylglucosamine, (6D) sialic acid and (6E) galactose all cause an increase in the binding of rheumatoid factor complexes to heat-aggregated IgG when compared to control (no added sugar or +glucose).
Figure 6B:
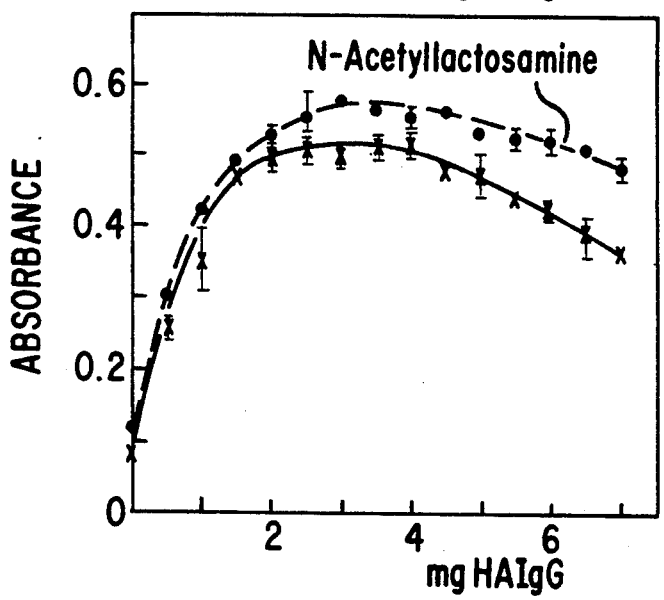
Figure 6C:
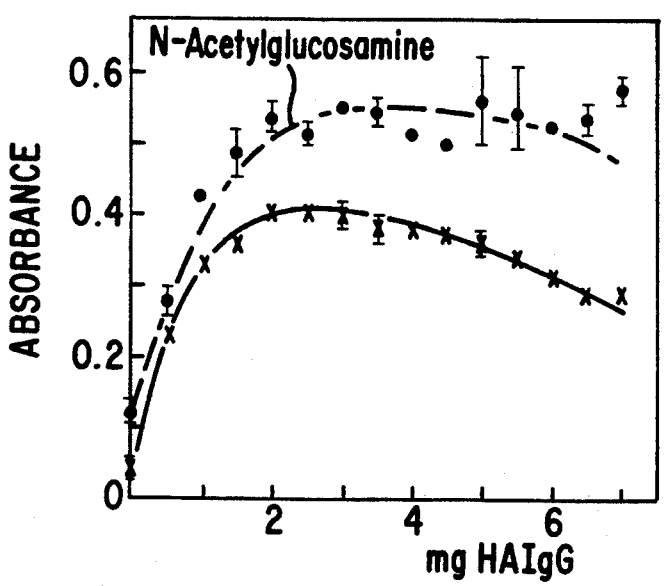
Figure 6D:
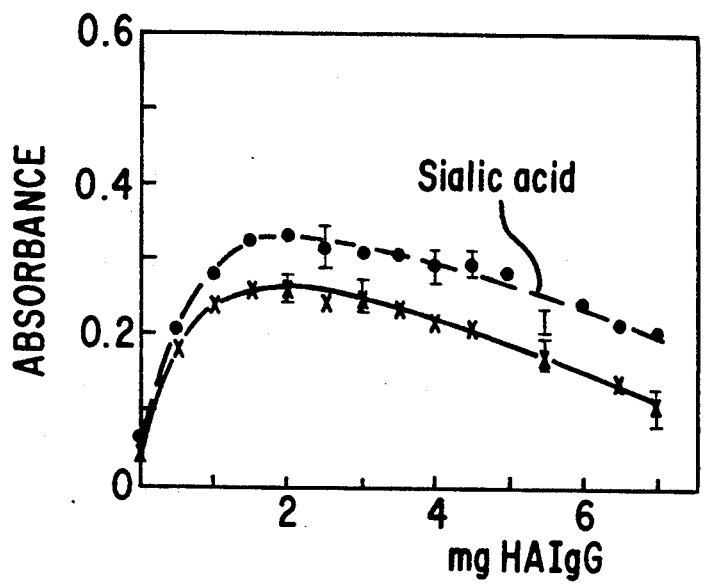
Figure 6E:
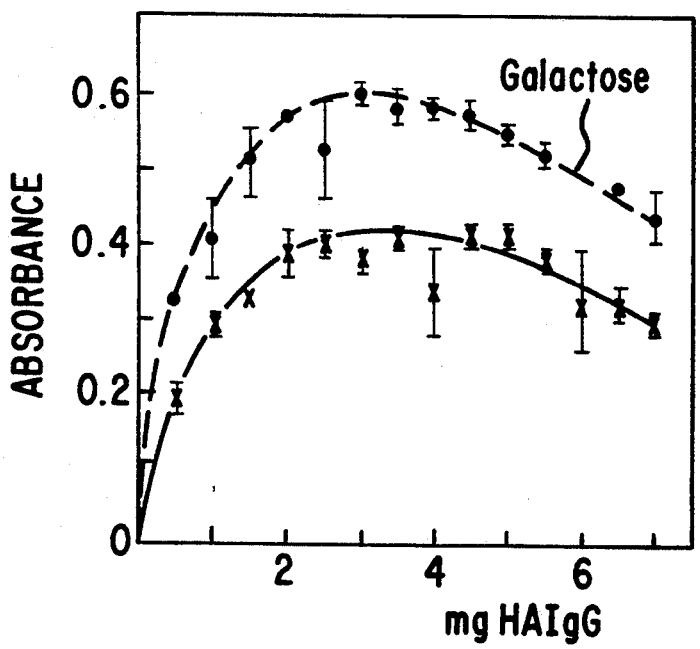

The results are shown in FIG. 4. The precipitin curve obtained from the sample containing sialyllactose was significantly lower than the curve for the control which contained no sialyllactose or other sugar. The amount of precipitate formed at equivalence was decreased by 17% in the sample containing sialyllactose. In a similar assay comparing glucose with control, FIG. 5, little or no effect upon the precipitin curve was observed for glucose.

(b) Identical assays were run as in (a) except that 10 mM of other sugars were used instead of 10 mM sialyllactose. The other sugars used for comparison with the oligosaccharide sialyllactose were the monosaccharides, glucose, N-acetylglucosamine, N-acetylneuraminic acid (sialic acid) and galactose, and the disaccharide, N-acetyllactosamine.

The results are shown in FIG. 6. The precipitin curves obtained from the samples containing these other sugars resulted in an increase in precipitate when compared to the curve for the control which contained no sugar.

It is thus seen that re-association of rheumatoid factors to form complexes was inhibited by the presence of sialyllactose but not by the other sugars.

EXAMPLE 3

Figure 7:
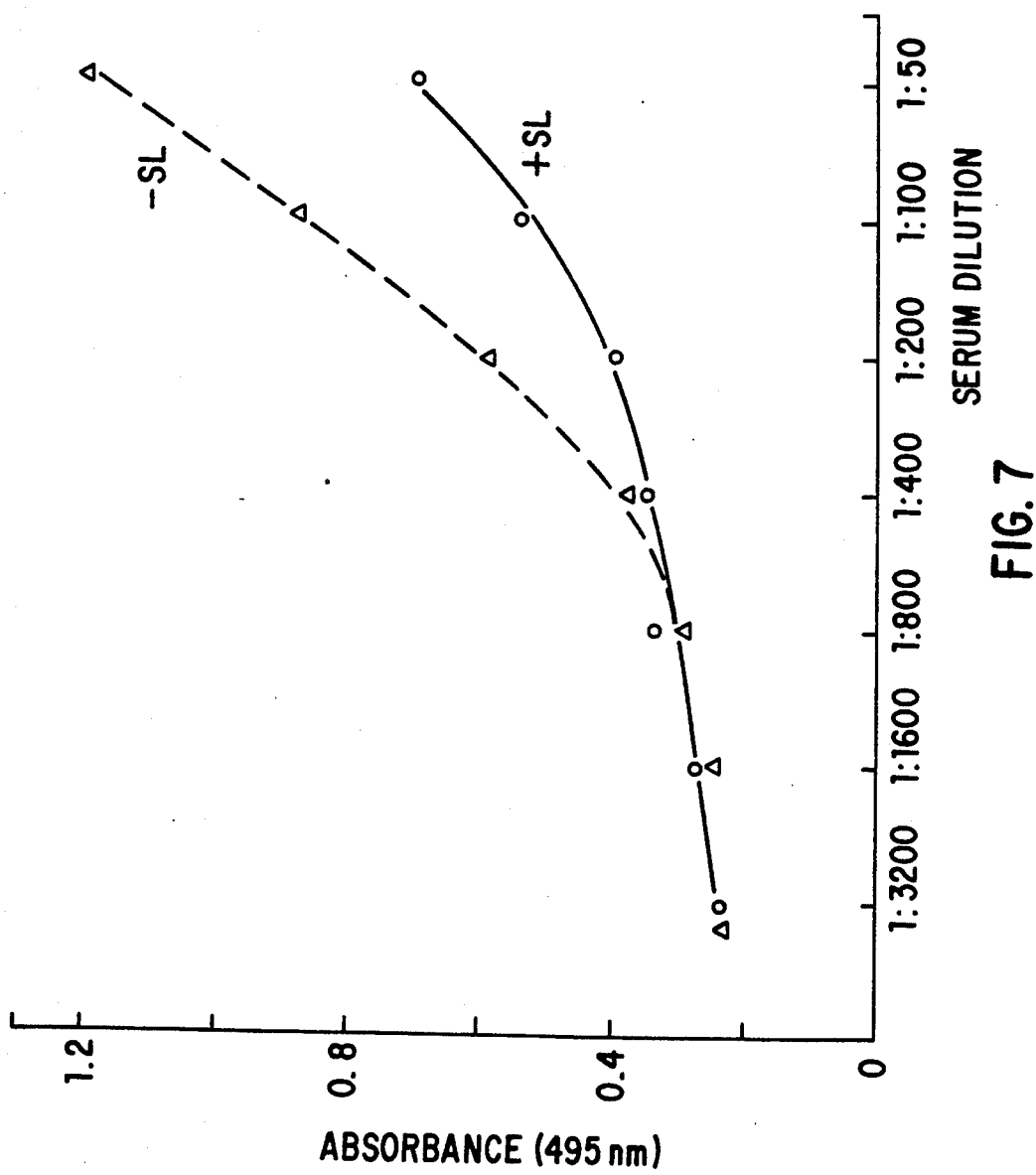
FIG. 7 is a graphical representation that shows the effect of sialyllactose (+SL) on rheumatoid factor in human serum compared to similar serum fluid samples without siallylactose (−SL), both at pH 7, when analyzed by a commercial ELISA (Melisa Rheumatoid HAII Immunoassay), in which absorbance at 495 nm is plotted against serum dilution.

The commercially-available Melisa Rheumatoid HAII Immunoassay Kit (Walker Laboratories Ltd., Cambridgeshire, England) was utilized to test directly whether or not siallactose/lactosamine (+SL) isomers can prevent the binding of anti-immunoglobulins to rheumatoid factors, i.e. prevent complex formation. FIG. 7 shows that in the presence of sialyllactose/lactosamine (+SL), less rheumatoid factor could be detected in the serum of a patient with rheumatoid arthritis than in similar serum in the absence of sialyllactose/lactosamine (−SL). Since immune-complex formation is concentration dependent, the effect of sialyllactose at the higher serum dilution shows this as a specific inhibitory effect. Results of the serum samples were read directly from a standard curve supplied by the manufacturer since the dilution factor of 1:100 is already included in the value stated on the standard labels.

EXAMPLE 4

This example illustrates the presence and availability of sialyllactose/lactosamine isomers in pregnancy sera from human sources. Pregnancy sera from human third trimester sources were screened by procedures which consisted of preparation of deproteinised serum samples and high performance anion exchange chromatography (HPEA) with pulsed amperometric detection (Dionex BioLC System). The general methodology of HPAE with PAD for the separation of positional isomers of oligosaccharides is described by Hardy and Townsend, Proc. Natl. Acad. Sci. U.S.A 85, 3289–3293 (1988); Townsend et al, Nature 35, 379–380 (1988). The following conditions were used in screening the pregnancy sera of this example:

Serum (100 μl) is diluted with 500 μl distilled water and 200 μl 0.3M barium hydroxide, vortexed and allowed to stand for 10 min at room temperature. After the addition of 200 μl of 0.18M zinc sulphate, the mixture was vortexed for 2 min and centrifuged at 1500 g. The resulting supernatant of 150 μl (equivalent to 15 μl serum) was chromatographed by HPAE (Dionex BioLC) using an eluant of 150 mM sodium hydroxide/100 mM sodium acetate, flow rate of 1 mL/min and utilizing triple pulsed amperometric detection.

Figure 8:
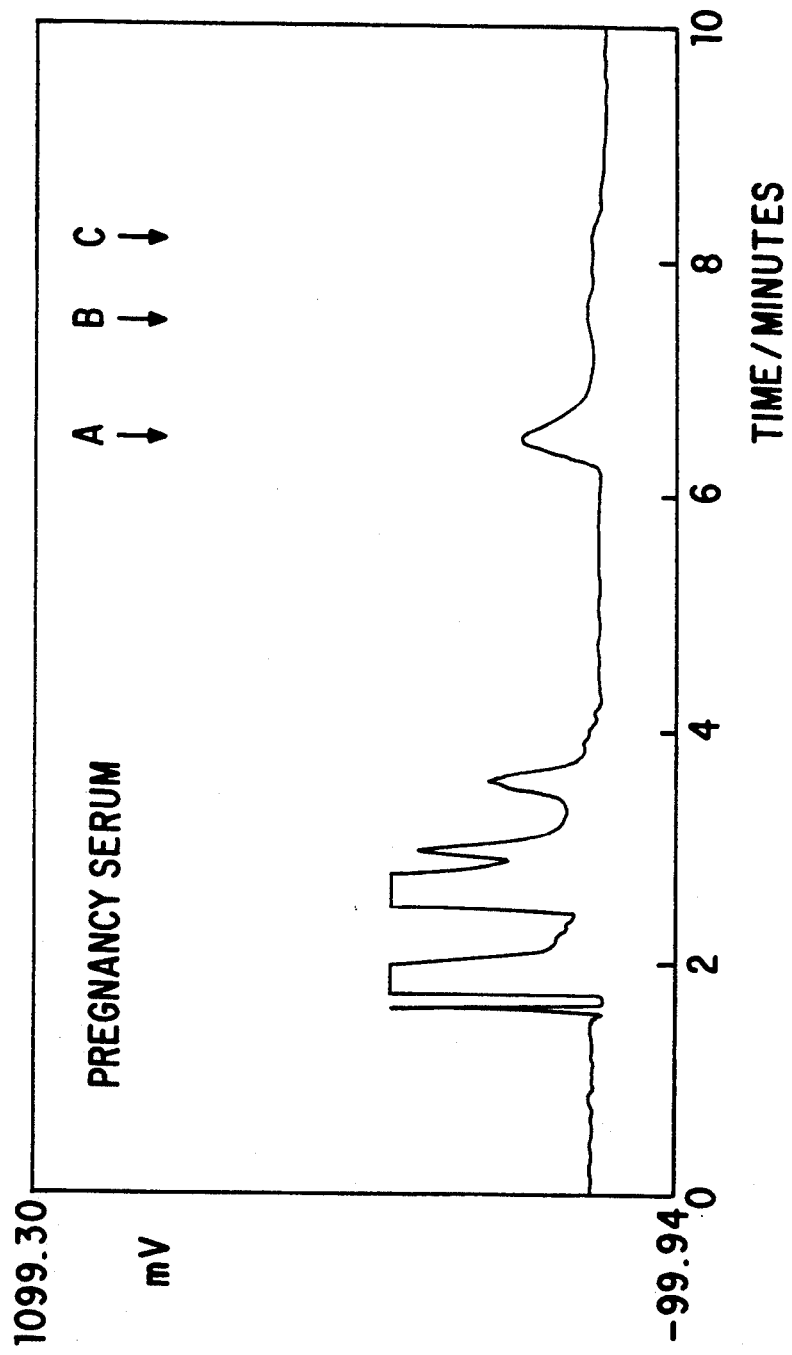
FIG. 8 is a graphical representation that shows the elution profile resulting from high performance anion exchange chromatography (HPEA) of human pregnancy serum using an eluant of 150 mM sodium hydroxide/100 mM sodium acetate, a flow rate of 1 mL/min and triple pulsed amperometric detection (Dionex BioLC System). A, B and C indicate the elution positions of compounds shown in Table I, below.

The results of this screening are shown in FIG. 8 and compared to results obtained in the analysis of sialyllactose/lactosamine isomers in colostrum as set forth in Table I. The results are expressed in percent of isomer and assume an equal response factor for the different isomers.

TABLE I

| Sera Source (Colostrum) | Peak A 6' sialyllactosamine | Peak B 6' sialyllactose or 3' sialyllactosamine | Peak C 3' sialyllactose |
|---|---|---|---|
| Sigma Bovine | 8% | 9%* | 83% |
| Sigma Human | trace | 77%* | 23% |
| Monsanto Bovine | 14% | 10%* | 76% |

*Predominantly 6' sialyllactose

The amount of the sialyllactose or other active oligosaccharide which would normally be administered therapeutically is primarily dependent upon the physical characteristics of the recipient and the severity of the arthritic conditions. The amount to be administered must be an effective amount, that is, an amount which is medically beneficial but does not present toxic effects which overweigh the advantages which accompany its use. Administration of the active oligosaccharide in physiologically acceptable solutions such as, for example, physiologic saline, is illustrative of a suitable parenteral solution of the oligosaccharide. According to Witt et al., Nutr. Metab. 23, 51–61 (1979), these oligosaccharides are orally absorbed intact. Other suitable formulations of the active oligosaccharide in pharmaceutically acceptable diluents or carriers in therapeutic dosage form can be prepared by reference to general texts in the pharmaceutical field such as, for example *Remington's Pharmaceutical Sciences*. Ed. Arthur Osol, 16th ed., 1980, Mack Publishing Co., Easton, Pennsylvania. An illustrative method of administration is by direct injection into the synovial fluid contained in the joint cavities, bursae and tendon sheaths of the rheumatoid arthritis patients. An illustrative effective amount of sialyllactose to dissociate immune complexes in the serum or synovial fluid of a rheumatoid arthritic patient and thereby release a relatively small protein having rheumatoid factor activity and a molecular weight of about 14 kDa as determined by SDS-PAGE under reducing conditions is about 10 μM. This protein contains the sequence (SEQ ID NO:1)

Phe Thr Ile Ser Arg Asn Asp Ser Lys Asn Thr Leu Tyr Leu
                5                        10 in which the asparagine in the Asn Asp Ser portion of the sequence is optionally glycosylated.

Various other examples will be apparent to the person skilled in the art after reading the foregoing disclosure without departing from the spirit and scope of the invention. It is intended that all such other examples be included within the scope of the appended claims.

---
SEQUENCE LISTING
---

(1) GENERAL INFORMATION:
    (i) APPLICANT: Rademacher, Thomas W.
                        Dwek, Raymond A.
    (ii) TITLE OF INVENTION: Use of Oligosaccacharides for Treatment of Arthritis
    (iii) NUMBER OF SEQUENCES: 1
    (iv) CORRESPONDENCE ADDRESS:
        (A) ADDRESSEE: Scott J. Meyer
        (B) STREET: 800 North Lindbergh Blvd.
        (C) CITY: St. Louis,
        (D) STATE: Missouri
        (E) COUNTRY: U.S.A
        (F) ZIP: 63043
    (v) COMPUTER READABLE FORM:
        (A) MEDIUM TYPE: Floppy disk
        (B) COMPUTER: IBM PC compatible
        (C) OPERATING SYSTEM: PC-DOS/MS-DOS
        (D) SOFTWEAR: PatentIn Release #1.24
    (vi) CURRENT APPLICATION DATA:
        (A) APPLICATION NUMBER:
        (B) FILING DATE:
        (C) CLASSIFICATION:
    (viii) ATTORNEY/AGENT INFORMATION:
        (A) NAME: Meyer, Scott J.
        (B) REGISTRATION NUMBER: 25,275
        (C) REFERENCE/DOCKET NUMBER: 07-27(496)A
    (ix) TELECOMMUNICATION INFORMATION:
        (A) TELEPHONE: (314) 694-3117

---
-continued
SEQUENCE LISTING
---

(2) INFORMATION FOR SEQ ID NO: 1:
    (i) SEQUENCE CHARACTERISTICS:
        (A) LENGTH: 14 amino acids
        (B) TYPE: amino acid
        (C) STRANDEDNESS: single
        (D) TOPOLOGY: linear
    (ii) MOLECULE TYPE: peptide
    (xi) SEQUENCE DESCRIPTION: SEQ ID NO: 1:

Phe Thr Ile Ser Arg Asn Asp Ser Lys Asn Thr Leu Tyr Leu
 1               5                       10

What is claimed:

1. A method for the treatment of a body fluid of an arthritic patient that contains immune complexes comprising exposing said body fluid to an exogenously administered silalyllactose or oligosaccharide mimitope of said sialyllactose containing a structural component that inhibits or disrupts the degree of occupancy of the Fc carbohydrate binding site on IgG to thereby dissociate said immune complexes.

2. The method of claim 1 in which the body fluid is serum.

3. The method of claim 1 in which the body fluid is that of a rheumatoid arthritis patient.

4. The method of claim 1 in which the oligosaccharide is sialyllactose.

5. The method of claim 2 in which the oligosaccharide is sialyllactose.

6. The method of claim 3 in which the oligosaccharide is sialyllactose.

7. The method of claim 1 in which the body fluid is the serum of a rheumatoid arthritis patient, and the oligosaccharide is sialyllactose.

8. The method of claim 1 in which the oligosaccharide is administered in pharmaceutically acceptable aqueous solution.

9. The method of claim 7 in which the oligosaccharide is administered in pharmaceutically acceptable aqueous solution.

10. A method of dissociating immune complexes in the serum or synovial fluid of a rheumatoid arthritis patient by treatment of said serum or synovial fluid with a small but effective amount of sialyllactose to thereby release a protein having rheumatoid factor activity and a molecular weight of about 14 kDa as determined by SDS-PAGE under reducing conditions and contains the sequency (SEQ ID NO:1)

Phe Thr Ile Ser Arg Asn Asp Ser Lys Asn Thr Leu Tyr Leu.
                5                       10

11. The method of claim 10 in which the amount of sialyllactose is 10 μM.

* * * * *